US00PP24764P2

(12) United States Plant Patent
Woolmore

(10) Patent No.: US PP24,764 P2
(45) Date of Patent: Aug. 12, 2014

(54) ***CORDYLINE* PLANT NAMED 'ROMA06'**

(50) Latin Name: ***Cordyline pumilio*×*C. banksii***
Varietal Denomination: ROMA06

(76) Inventor: Malcolm Woolmore, Whenuapal (NZ)

( * ) Notice: Subject to any disclaimer, the term of this patent is extended or adjusted under 35 U.S.C. 154(b) by 520 days.

(21) Appl. No.: 12/931,831

(22) Filed: Feb. 11, 2011

Related U.S. Application Data

(60) Provisional application No. 61/338,285, filed on Feb. 16, 2010.

(51) Int. Cl.
*A01H 5/00* (2006.01)

(52) U.S. Cl.
USPC ..... Plt./383

(58) Field of Classification Search
USPC ..... Plt./383
See application file for complete search history.

(56) References Cited

U.S. PATENT DOCUMENTS

| | | | | |
|---|---|---|---|---|
| PP14,224 | P3 * | 10/2003 | Jury et al. | Plt./383 |
| PP16,954 | P2 * | 8/2006 | Parthasarathy et al. | Plt./226 |
| PP18,545 | P3 * | 3/2008 | Jewell | Plt./383 |
| PP20,634 | P3 * | 1/2010 | Rendle | Plt./383 |
| PP21,220 | P2 * | 8/2010 | Topping | Plt./383 |
| PP22,345 | P2 * | 12/2011 | Chen | Plt./383 |
| PP23,190 | P2 * | 11/2012 | Chen | Plt./383 |
| PP23,503 | P3 * | 3/2013 | Drane et al. | Plt./383 |
| PP23,512 | P3 * | 4/2013 | Benzur | Plt./383 |

OTHER PUBLICATIONS

Jury, Abbie. "Cordyline Red Fountain" Tikorangi The Jury Garden Nov. 11, 2011 available at jury.co.nz/tag/cordyline-red-fountain/ accessed Aug. 14, 2013.*
Anonymous. "Trial of Cordyline 2002-2004 An Invited RHS Trial" The Trials Office, The Royal Horticultural Society 2004.*
Woolmore. Australian Plant Breeders Rights Image Cordyline 'Roma 06' available at http://pericles.ipaustralia.gov.au/pbr_db/image-detail.cfm?AID=10725109.*
UPOV Pluto AU citation for 'ROMA 06' Mar. 30, 2011.*
Woolmore. AU PBR application details application 2010/325 'Roma 06'.*
UPOV Pluto NZ PBR Citation for 'ROMA 06' Jul. 14, 2010.*
NZ PBR Objective Description of Variety 'BURGUNDY' Jul. 14, 2010.*
UPOV Pluto QZ Citation for 'ROMA 06' Apr. 15, 2012.*
Anonymous. San Marcos Growers. "Cordyline" accessed Aug. 14, 2013 available at http://www.smgrowers.com/info/cordyline.asp.*

* cited by examiner

*Primary Examiner* — Wendy C Haas

(57) ABSTRACT

A new and distinct cultivar of *Cordyline* named 'ROMA06' that is characterized by tight rapidly clumping habit and sword-like leaves that are burgundy-red in color. In combination these traits set 'ROMA06' apart from all other existing varieties of *Cordyline* known to the inventor.

4 Drawing Sheets

Genus: *Cordyline.*
Species: *C. pumilio*×*C. banksii.*
Denomination: 'ROMA06'.

BACKGROUND OP THE INVENTION

The present invention relates to a new and distinct cultivar of *Cordyline*, commonly known as cabbage tree or cabbage palm, which is grown as a specimen architectural plant for use in container, border, and modern landscape. Cabbage palms eventually flower, however they are most valued for their attractive foliage, that is enhanced when backlit. The new cultivar from the family *Agavaceae* is known botanically as *Cordyline pumilio*×*C. bunksii* and will be referred to hereinafter by the cultivar name 'ROMA06'.

'ROMA06' arose from a breeding program that has been established by the inventor at the inventor's nursery in Whenuapai, New Zealand. The objective of the breeding program is to produce a series of new *Cordyline* varieties that exhibit broad leaves, novel foliage color, and naturally tight, rapidly clumping habit.

'ROMA06' resulted from the deliberate pollination of the female parent, an individual *Cordyline pumilio* (species, unpatented) and the male parent, an individual *Cordyline banksii* (species, unpatented). During the breeding process the parents were placed in an isolated environment. Pollen from the male parent was transferred to the stigma of the female parent. Resulting seed was germinated and planted out by the inventor. The inventor selected 'ROMA06' as a single plant in 2007 based on the criteria of broad leaves, habit, and foliage color.

'ROMA06' may be compared with its parents as follows. Whereas the female parent species grows as a very tight clump of short spiky little leaves, the growth habit of 'ROMA06' is more open, taller and arching. Whereas the male parent species is very vigorous and quickly achieves a height of 3 meters with a single trunk, 'ROMA06' grows with multiple trunks and does not exceed a height of 2 meters. The differences between 'ROMA06' and its parents become increasingly apparent with age.

The variety of *Cordyline* which the inventor considers to be closest in characteristics to 'ROMA06' is *Cordyline* plant named 'JURred' (U.S. Plant Pat. No. 14,224). The two varieties may be compared by the width of their leaves. Whereas the leaves of 'ROMA06' are less than 2 cm in width, the leaves of 'JURred' range between 2 cm and 4 cm in width. In addition, the inventor considers that 'ROMA06' more quickly forms a clump with more basal shoot growth than 'JURred'. The differences between 'ROMA06' and 'JURred' become increasingly apparent with age.

The distinguishing characteristics of 'ROMA06' include light clumping habit and sword-shaped leaves that are burgundy-red in color. After 4 years 'ROMA06' achieves a height and width of 0.8 meters with multiple small trunks and white vanilla-scented flowers. Cultural requirements include full sun to partial shade, moderate watering during the growing season which is then reduced in fall and winter. 'ROMA06' is asexually propagated by the methods of division and tissue culture. 'ROMA06' is hardy in USDA Zone 8.

The inventor first propagated the selected single seedling plant of 'ROMA06' in 2007 using the method of division. Subsequently 'ROMA06' has been propagated under the inventor's direct supervision by the method of tissue culture. The plants resulting from the first, and from all subsequent generations, have exhibited the identical characteristics as the inventor's original selection. The inventor has determined that 'ROMA06' is stable, uniform, and reproduces true to type in successive generations of asexual propagation.

SUMMARY OF THE INVENTION

The following traits have been repeatedly observed and represent the distinguishing characteristics of 'ROMA06'. In combination these traits set 'ROMA06' apart from all other existing varieties of *Cordyline* known to the inventor. 'ROMA06' has not been tested under all possible conditions and phenotypic differences may be observed with variations in environmental, climatic, and cultural conditions without however any variance in genotype.

1. 'ROMA06' grows with a tight rapidly clumping habit.
2. The foliage of 'ROMA06' is broad in comparison with typical varieties of the genus and is burgundy-red in color.
3. After 4 years of growth, a plant of 'ROMA06' achieves a height and width of 0.8 meters and has formed multiple trunks.
4. At 4 years of growth, 'ROMA06' is free-flowering with blooms that are pleasantly scented with a vanilla-like fragrance.
5. 'ROMA06' grows well in moist well-drained soils in full sun to partial shade.
6. 'ROMA06' is hardy to USDA Zone 8.

BRIEF DESCRIPTION OF THE DRAWINGS

The accompanying color drawings illustrate the overall appearance of 'ROMA06' showing the color as true as is reasonably possible to obtain in color reproductions of this type. Color in the drawings may differ from color values cited in the detailed botanical description, which accurately describe the actual color of 'ROMA06'.

The drawing labeled

The drawing labeled

The drawing labeled

The drawing labeled

Figure 1:
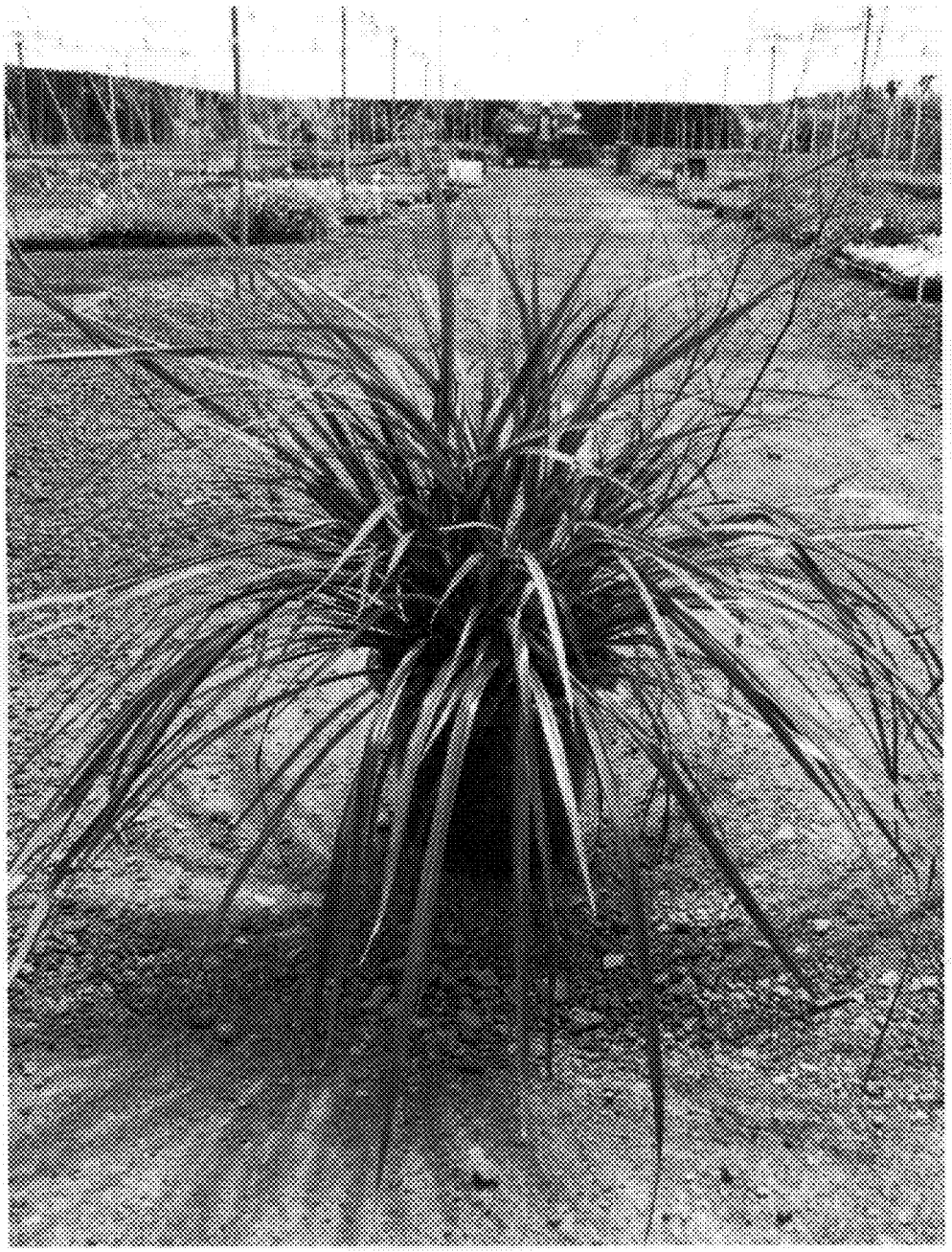
FIG. 1 depicts a four-year-old plant of 'ROMA06' which has been grown out-of-doors in a 15-gallon container in Auckland, New Zealand.
Figure 2:
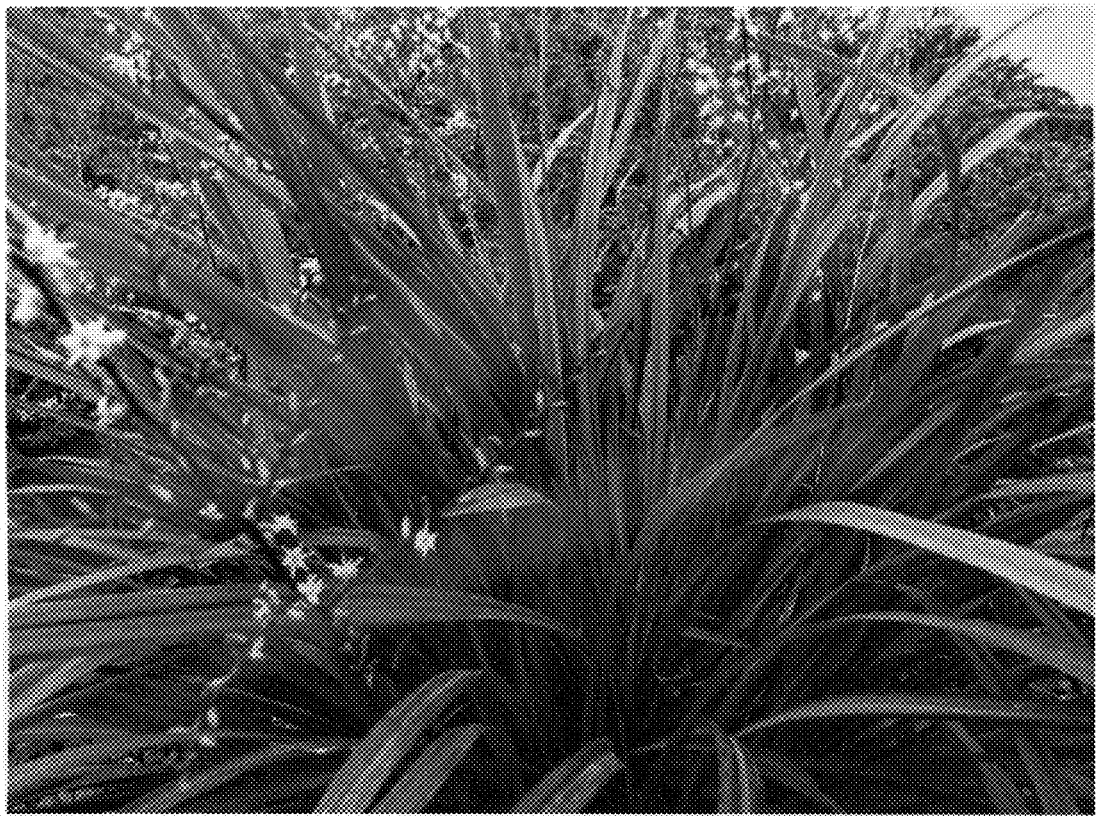
FIG. 2 presents a close up view of the same plant which is illustrated in FIG. 1. The plant has produced its first inflorescence.
Figure 3:
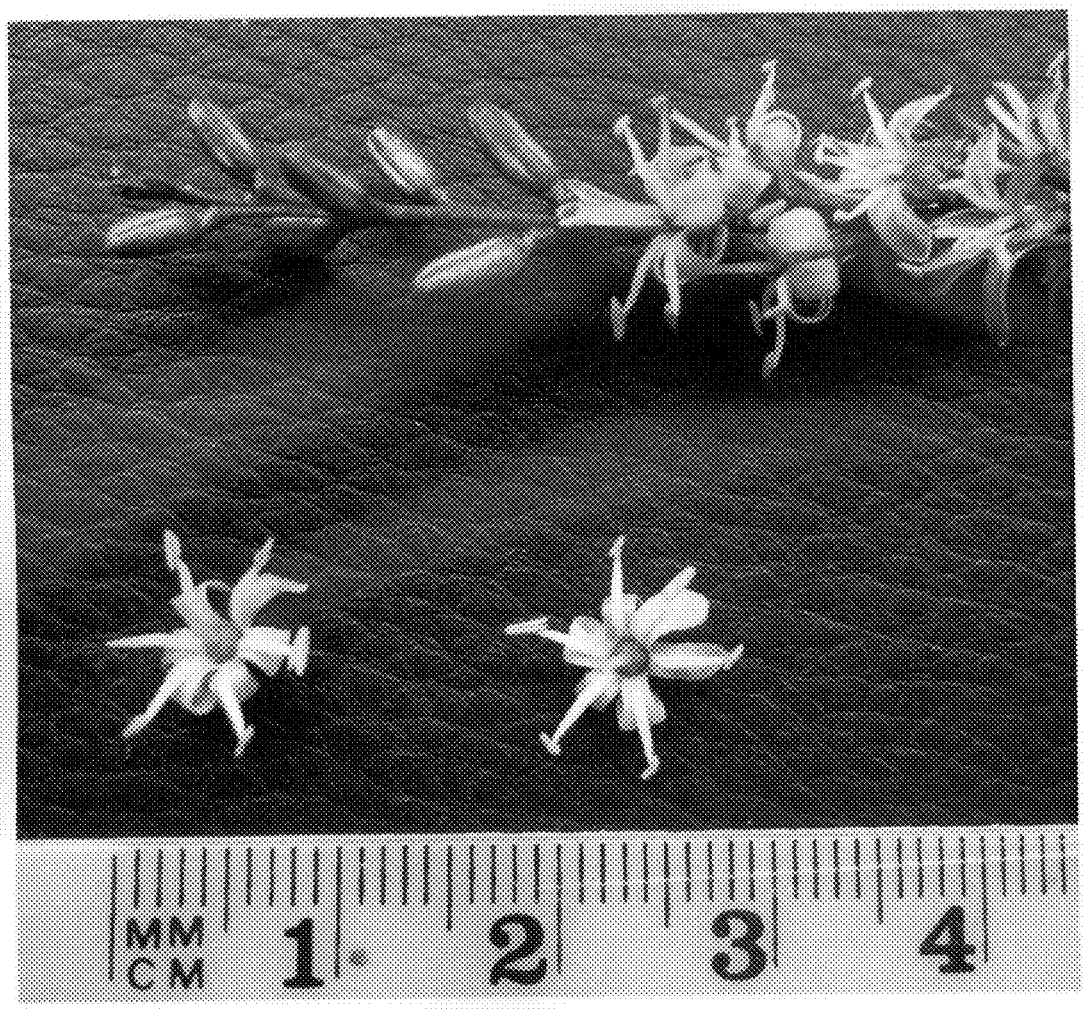
FIG. 3 depicts the inflorescence of 'ROMA06' in bud and flower of 'ROMA06'. Two fully expanded flowers have been detached.
Figure 4:
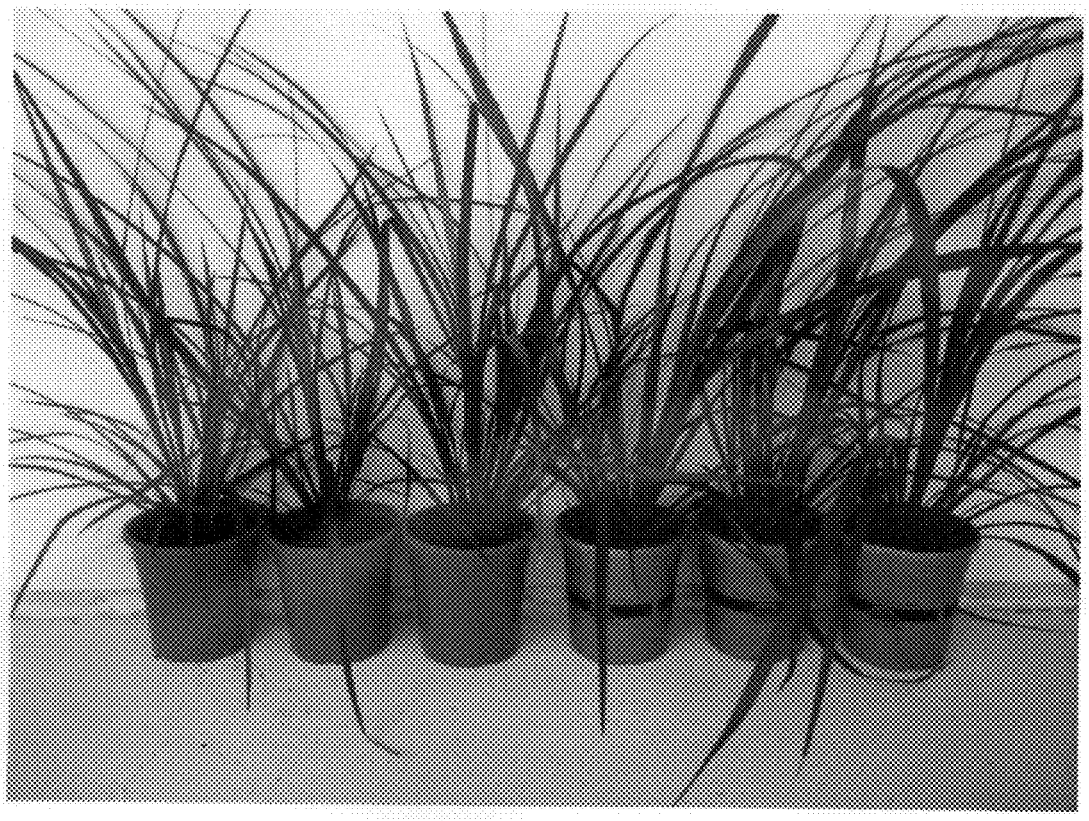
FIG. 4 presents a comparison between 'ROMA06' (shown on the left of the drawing and growing in blue colored containers) and the *Cordyline* variety 'JURred' (shown on the right of the drawing and growing in the gold colored containers). In particular, this drawing depicts the characteristic difference in leaf width between the two varieties. All of the illustrated plants have been grown under identical conditions out of doors in Melbourne, Australia and are of the same age, approximately nine months from transplanting of a rooted plug from tissue cultured propagation.

All drawings were made using conventional techniques and although color may appear different from actual color due to light reflectance, they are as accurate as possible by conventional photography.

BOTANICAL DESCRIPTION OF THE PLANT

The following is a detailed botanical description of 'ROMA06'. Observations, measurements, values and comparisons were collected in Arroyo Grande, Calif., from a 36-month-old 2-gallon container plant growing out-of-doors. Color determinations are made in accordance with The 2001 Royal Horticultural Society Colour Chart from London, England, except where general color terms of ordinary dictionary significance are used. The growing requirements of 'ROMA06' are similar to the species.

Botanical classification: *Cordyline pumilio*×*C. bunksii* 'ROMA06'.

Family: *Agavaceae.*

Common name: Cabbage tree or cabbage palm.

Habit: Tight clumping habit.

Plant form: Weeping.

Commercial category: Architectural specimen.

Use: Container, garden border, and modern landscape.

Suggested commercial container size: 2-gallon container.

Parentage: 'ROMA06' is a hybrid plant that arose from the deliberate cross-pollination of the following patents:

*Female parent.*—An individual *Cordyline pumilio* (unpatented).

*Male parent.*—An individual *Cordyline banksii* (unpatented).

Propagation method: Division and tissue culture using micropropagation of shoot tips and meristems.

Rooting system: Thick and fibrous.

Vigor (range): Slow to moderate.

Time to develop roots (average): 2 months in vitro by tissue culture.

Crop time (average): 3 months required in plug or liner stage before potting into a 2-gallon container.

Crop time (range): 15 to 18 months from tissue culture to produce a 2-gallon container plant.

Plant dimensions (first season): 0.3 meters in height and 0.3 meters in width from tissue culture.

Plant dimensions (at 4 years): 0.8 meters in height and 0.8 meters in width.

Cultural requirements: Grow in full sun to part shade, well-draining loam soil, with moderate water. Drought tolerant once established.

Pest or disease resistance: None known to the inventor.

Pest or disease susceptibility: None known to the inventor.

Hardiness: Hardy to USDA Zone 8.

Caudex:

*Branching.*—Basal.

*Quantity* (*average*).—1 at 12 months and 4 at 4 years.

*Surface.*—Imbricate leaves that give way to petioles.

*Texture* (*range*).—Fleshy to woody.

*Shape.*—Stout sub-cylindrical.

*Color.*—187A.

*Length* (*range*).—10-15 cm.

*Diameter* (*range*).—1-1.50 cm.

Foliage:

*Type*.—Evergreen.

*Leaf arrangement*.—Spiral.

*Leaf quantity* (*average*).—70 per 2-gallon container.

*Leaf texture*.—Coreaceous.

*Leaf division*.—Simple.

*Leaf margin*.—Entire.

*Leaf appearance* (*abaxial surface*).—Matte.

*Leaf appearance* (*adaxial surface*).—Semi-glossy.

*Leaf surface* (*abaxial and adaxial*).—Glabrous.

*Leaf shape* (*range*).—Broad linear to sword-like.

*Leaf length* (*range*).—72 cm. to 86 cm.

*Leaf width* (*average*).—1.75 cm.

*Leaf color* (*adaxial surface*).—187A.

*Leaf color* (*abaxial surface*).—N186C.

*Leaf apex* (*range*).—Sharply acuminate to cirrhose.

*Leaf base*.—Truncate.

*Venation pattern*.—Parallel.

*Vein color*.—182D.

*Mid-vein*.—Conspicuous.

*Mid-vein color* (*abaxial and adaxial surfaces*).—N186D.

*Attachment* (*range*).—Sheathing to petiolate.

*Petiole shape*.—Concave in cross-section.

*Petiole surface*.—Glabrous and minutely ribbed.

*Petiole color*.—N186C.

*Petiole dimensions* (*average*).—8 cm in length and 0.60 cm in width.

*Leaf fragrance*.—None observed.

Inflorescence:

*Inflorescence*.—Terminal panicle with branches below.

*Inflorescence quantity* (*average*).—3 per 15-gallon container plant.

*Inflorescence length* (*average*).—45 cm.

*Flowers*.—

*Flower color*.—N155B and 186D.

*Flower attachment*.—Subsessile.

*Aspect*.—Facing upward and outward.

*Flower number* (*inflorescence fully developed*).—Approximately 100.

*Flower dimensions* (*average*).—1 cm in diameter and 0.70 cm in depth. Tepals: 6 in number. Fused or unfused: Fused at base to form short perianth tube. Tepal color (abaxial surface.): N155B and 186D. Tepal color (adaxial surface): N155B and 186D. Tepal dimensions (average): 4 mm in length and 2 mm in width. Tepal shape: Oblong. Tepal form: Recurved. Tepal margin: Entire. Tepal apex: Rounded. Tepal base: Truncate. Perianth tube dimensions (average): 2 mm in height and 2 mm in diameter. Perianth tube shape: Urn-shaped. Perianth tube color (dorsal surface): 186C. Perianth tube surface (dorsal surface): Glabrous. Blooming season: Summer to late fall. Scape dimensions (average): >4.50 cm in length and 1 mm in diameter. Scape color: 179A. Scape surface: Glabrous. Scape shape: Cylindrical. Quantity of buds (average per scape): 8 in number. Quantity of flowers (average per scape): 10 in number. Bud color: 182A (182D-183D range). Bud dimensions: 0.60 cm in length and 2 mm in width. Bud surface: Glabrous. Bud apex: Rounded. Bud base: Rounded.

*Inflorescence fragrance*.—Vanilla-like fragrance.

Reproductive organs:

*Stamen quantity*.—6 in number.

*Stamen shape*.—Flattened filament.

*Stamen attachment*.—Adnate to perianth tube.

*Stamen length*.—4 mm.

*Stamen color*.—155D.

*Pollen quantity*.—Moderate.

*Pollen color*.—3C.

*Anther quantity*.—6 in number.

*Anther attachment*.—Versatile.

*Anther length*.—1 mm.

*Anther color*.—3A.

*Pistil*.—1 in number.

*Pistil length*.—0.50 cm.

*Ovary position*.—Superior.

*Ovary color*.—151C.

*Ovary shape*.—Globose.

*Ovary diameter*.—1.50 mm.

The invention claimed is:

1. A new and distinct cultivar of *Cordyline* plant named 'ROMA06' as described and illustrated herein.

* * * * *